United States Patent [19]

Brown et al.

[11] Patent Number: 5,095,038
[45] Date of Patent: Mar. 10, 1992

[54] CARBOCYCLIC COMPOUNDS USEFUL AS LEUKOTRIENE ANTAGONISTS

[75] Inventors: Frederick J. Brown, Newark, Del.; Thomas P. Maduskuie, Jr., Wilmington, Del.; Victor G. Matassa, Essex, England; Ying K. Yee, Kennett Square, Pa.

[73] Assignee: ICI Americas Inc., Wilmington, Del.

[21] Appl. No.: 336,976

[22] Filed: Apr. 12, 1989

Related U.S. Application Data

[63] Continuation-in-part of Ser. No. 181,333, Apr. 14, 1988, abandoned.

[51] Int. Cl.⁵ ............... A61K 31/535; C07D 295/112
[52] U.S. Cl. ..................... 514/604; 514/237.5; 514/255; 514/319; 514/423; 544/159; 544/391; 546/205; 548/540; 560/315
[58] Field of Search ............ 544/159, 391; 546/205; 548/540; 560/315; 514/237.5, 255, 319, 423, 604

[56] References Cited

U.S. PATENT DOCUMENTS

| 3,574,741 | 4/1971 | Gould et al. | 564/84 |
| 4,401,663 | 9/1983 | Buckwalter et al. | 564/84 |
| 4,631,287 | 12/1986 | Chakraborty et al. | 514/307 |

FOREIGN PATENT DOCUMENTS

0179619 10/1985 European Pat. Off. .

OTHER PUBLICATIONS

G. W. Taylor & S. R. Clarke, *Trends in Pharmacological Science*, (1966) 7, 100–103.
J. L. Marx, *Science*, (1982) 215, 1380: "The Leukotrienes in Allergy and Inflammation".
J. A. Cook et al., *J. Pharm. Exp. Ther.* (1985) 235, 470: "Protective Effective of a Selective Leukotriene Antagonist in Endotoxemia in the Rat".
C. Denzlinger et al., *Science* (1985) 230, 330: "Leukotrienes as Mediators in Tissue Trauma".
R. D. Krell, *J. Pharm. Exp. Ther.* (1979) 211, 436: "Pharmacologic Characterization of Isolated Rhesus Monkey Brochial Smooth Muscle".
D. Aharony et al., *Fed. Proc.*(1987) 46, 691: "Inhibition of $^3$H-Leukotriene (LT) D$_4$ Binding to Guinea-Pig Lung Membrane Receptors by the Novel Leukotriene Antagonist ICI 198,615".
Yung-chi Cheng and W. H. Prusoff, *Biochem. Pharmacol.* (1973) 22, 3099–3108: "Relationship Between the Inhibition Constant (K$_j$) and the Concentration of Inhibitor Which Causes 50 Percent Inhibition (I$_{50}$) of an Enzymatic Causes 50 Reaction".
R. F. Heck et al., *J. Org. Chem.* (1974) 39, 3327.
J. F. Fauvarque et al., *J. Organometallic Chem.* (1979) 177, 273.
Z. Yoshida et al., *Tet. Letters* (1986) No. 27, 955.
F. A. Davis et al., *J. Amer. Chem. Soc.* (1979) 101, 1044.
E. Keinan et al., *J. Org. Chem.* (1983) 48, 1772.
B. Akermark et al., *Organometallics* (1984) 3, 679.
C. K. Ingold and H. A. Piggott, *J. Chem. Soc.* (1923) 123, 1469.

*Primary Examiner*—Mary C. Lee
*Assistant Examiner*—Jacqueline Haley
*Attorney, Agent, or Firm*—Rosemary M. Miano; Thomas E. Jackson

[57] ABSTRACT

This invention comprises novel carbocyclic compounds of formula I (wherein A, Z, R$^{11}$ and R$^{12}$ are defined in the specification) derived from acylsulfonamide derivatives of α-carbocyclyltoluic acids wherein said compounds of formula I antagonize the actions of one or more of the arachidonic acid metabolites known as leukotrienes. The invention also provides pharmaceutically acceptable salts of the formula I compounds; pharmaceutical compositions containing the formula I compound, or their salts, for use in the treatment of, for example, allergic or inflammatory diseases, or endotoxic or traumatic shock conditions; and processes for the manufacture of the formula I compounds, as well as intermediates for use in such manufacture.

11 Claims, No Drawings

CARBOCYCLIC COMPOUNDS USEFUL AS LEUKOTRIENE ANTAGONISTS

This application is a continuation-in-part of U.S. Ser. No. 07/181,333, filed Apr. 14, 1988, and now abandoned.

SUMMARY AND BACKGROUND OF THE INVENTION

This invention concerns novel carbocyclic compounds and, more particularly, novel carbocyclic compounds derived from acylsulfonamide derivatives of α-carbocyclyltoluic acids, which antagonize the pharmacological actions of one or more of the arachidonic acid metabolites known as leukotrienes (hereafter referred to as "leukotriene antagonist properties"). The novel derivatives are useful whenever such antagonism is desired. Thus, such compounds may be of value in the treatment of those diseases in which leukotrienes are implicated, for example in the treatment of allergic or inflammatory diseases, or of endotoxic or traumatic shock conditions. The invention also provides pharmaceutical compositions containing the novel derivatives for use in such treatments, and processes and intermediates for the manufacture of the novel derivatives.

In European Patent Application publication number 0 179 619 A1 are disclosed N-acylated derivatives of a series of indoles, indazoles and indolines having an amino group in the benzenoid ring and which possess leukotriene antagonizing properties. We have now discovered a series of bicyclic carbocyclic compounds which have an amidic substituent in a benzenoid ring and a benzyl substituent in the other ring, and which unexpectedly possess the property of antagonizing one or more of the arachidonic acid metabolites known as leukotrienes; this is the basis for our invention.

DESCRIPTION OF THE INVENTION

According to the invention there is provided a compound of formula I (formula set out, together with other formulae denoted by Roman numerals, on pages following the Examples) wherein —Z— is selected from a group consisting of (a) —C($R^9$)=CH— and (b) —CH($R^9$)—;

A is an amidic side chain selected from a group consisting of (i) an acylamino group of formula $R^1$.W CO.NH-, (ii) a carboxamido group of formula $R^1$.NH CO-, and (iii) an aliphatic carboxamidic group of formula $R^1R^2$N.CO.M-; and wherein $R^1$ is hydrogen or (1–6C)alkyl optionally containing a double or triple bond and $R^2$ is selected from a group consisiting of hydrogen, (1–6C)alkyl optionally containing a double or triple bond, (3–6C)cycloalkyl, (3–6C)cycloalkyl(1–3C)alkyl and phenyl, in which a cycloalkyl group or the cycloalkyl portion of a cycloalkylalkyl group may optionally contain a double bond and may optionally bear 1 or 2 (1–3C)alkyl groups, or $R^1$ and $R^2$, together with the nitrogen atom to which they are attached, form a pyrrolidino, piperidino, piperazino, 4-[(1–3C)alkyl]piperazino, or morpholino group;

M is a (1–5C)alkylene group;

W is oxy, imino or a direct link to $R^1$;

$R^9$ is selected from a group consisting of hydrogen, (1–6C)alkyl optionally containing a double or triple bond, (1–5C)alkoxy, (1–6C)alkanoyl and halogeno;

$R^{11}$ is hydrogen or (1–4C)alkoxy; and $R^{12}$ is phenyl, which may optionally bear 1 or 2 substituents selected from a group consisting of halogeno, methyl and (1–4C)alkoxy;

and the salts thereof, especially pharmaceutically acceptable salts.

It will be appreciated that certain of the compounds of formula I, for example those wherein $R^1$ contains an asymmetrically substituted carbon atom, may exist in, and be isolated in, optically-active and racemic forms. In addition, it will be appreciated that certain compounds of formula I, may exist in, and be isolated in, separate stereoisomeric forms. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine the leukotriene antagonist properties by the standard tests described hereinafter.

In this specification Ra, Rb, $R^1$ et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Halogeno is fluoro, chloro, bromo or iodo.

Particular values for the generic radicals described as ranges above under $R^1$, $R^2$ et cetera are as follows:

Particular values for $R^1$, $R^2$ or $R^9$ when it is (1–6C)alkyl include, for example, methyl, ethyl, propyl, isopropyl, butyl, 1-methylpropyl, 2-methylpropyl, pentyl, 1-ethylpropyl, 3-methylbutyl, hexyl, and 4-methylpentyl; and when the alkyl group contains an optional double or triple bond, particular values include allyl, 2-methylprop-2-enyl, 3-methylbut-3-enyl and 2-propynyl.

Particular values for $R^2$ when it is (3–6C)cycloalkyl include, for example, cyclopropyl, cyclobutyl, cyclopentyl, and cyclohexyl; and when the cycloalkyl group contains an optional double bond or alkyl substituent, particular values include cyclopentenyl, cyclohexenyl and methylcyclobutyl.

Particular values for $R^2$ when it is (3–6C)cycloalkyl(1–3C)alkyl include, for example, cyclopropylmethyl, cyclobutylmethyl, cyclopentylmethyl, cyclohexylmethyl, 1-cyclopentylethyl and 2-cyclopentylethyl; and when the cycloalkyl portion contains an optional double bond or alkyl substituent, particular values include methylcyclopentylethyl.

Particular values for a (1–3C)alkyl substituent when $R^1$ and $R^2$, together with the nitrogen atom to which they are attached, form a 4-[(1–3C)]alkylpiperazino group, include, for example, methyl, ethyl and isopropyl.

Particular values for M include, for example, methylene, ethan-1,2-diyl, propan-1,3-diyl, propan-1,2-diyl, 2-methylpropan-1,2-diyl, butan-1,3-diyl and butan-1,4-diyl.

Particular values for $R^9$ when it is (1–5C)alkoxy include, for example, methoxy, ethoxy, propoxy, 2-methylpropyloxy, butoxy, pentoxy and 3-methylbutoxy.

Particular values for $R^9$ when it is (1–6C)alkanoyl include, for example, acetyl, propanoyl, butanoyl, 2-methylpropanoyl, and 3-methylbutanoyl.

Particular values for $R^9$ when it is halogeno, include for example, bromo and chloro.

Particular values for $R^{11}$ when it is (1–4C)alkoxy include, for example, methoxy, ethoxy and propoxy;

Particular values for an optional substituent on $R^{12}$ when the substituent is halogeno include, for example, chloro and bromo; and when the substituent is (1–4C)alkoxy, methoxy and ethoxy.

It is preferred that an optional substituent on $R^{12}$ be at the 2-position.

Typical values for the radicals and groups for a compound of formula I are independently selected from those listed below.

A typical value for A when A is an acylamino group of formula $R^1.W.CO.NH-$ is cyclopentylacetamido.

Typical values for A when A is a carboxamido group of formula $R^1.NH.CO-$ include carboxamido, 2-methylpropylcarboxamido, 2-methylbutylcarboxamido and 2-ethylbutylcarboxamido.

Typical values for A when A is an aliphatic carboxamido group of formula $R^1R^2N.CO.M-$ include 2-(propylcarbamoyl)propyl, 3-(dimethylcarbamoyl)propyl, 4-(dimethylcarbamoyl)butyl and 4-morpholino-4-oxobutyl.

It will be appreciated that within the above definitions there are included a number of sub-groups of compounds, for example:

(a) napthalenes of formula Ia and
(b) indenes of formula Ib;

and wherein, in each sub-group, A, $R^9$, $R^{11}$ and $R^{12}$ have any of the above defined meanings; together with the pharmaceutically acceptable salts thereof.

Preferred compounds of the invention include 4-[7-(cyclopentylacetamido)naphth-1-ylmethyl]-3-methoxy-N-(2-methylphenylsulfonyl)benzamide; 4-[7-(3-dimethylcarbamoylpropyl)naphth-1-ylmethyl]-3-methoxy-N-(2-methylphenylsulfonyl)benzamide; 4-[6-(cyclopentylacetamido-3H-inden-1-ylmethyl]-3-methoxy-N-(2-methylphenylsulfonyl)benzamide; 3-methoxy-N-(2-methylphenylsulfonyl)-4-[7-(2-methylpropylcarbamoyl)naphth-1-ylmethyl]benzamide; and 3-methoxy-4-[7-(2-methylbutylcarbamoyl)naphth-1-ylmeth-yl]-N-(2-methylphenylsulfonyl)benzamide.

Specific compounds of the invention are described in the accompanying examples and may be used either in the free acid form or as a corresponding pharmaceutically acceptable salt.

Examples of suitable pharmaceutically acceptable salts are salts formed with bases which form a physiologically acceptable cation, such as alkali metal (especially sodium and potassium), alkaline earth metal (especially calcium and magnesium), aluminum and ammonium salts, as well as salts made with appropriate organic bases such as triethylamine, morpholine, piperidine and triethanolamine.

The compounds of formula I may be made by processes which include processes well known in the chemical art for the production of structurally analogous carbocyclic compounds. Such processes for the manufacture of a compound of formula I as defined above are provided as further features of the invention and are illustrated by the following procedures in which the meanings of generic radicals are as defined above, U is defined as a suitable leaving group, for example, halogeno (especially chloro, bromo, or iodo) or alkane- or arene-sulfonyloxy (especially trifluoromethanesulfonyloxy, methanesulfonyloxy or p-toluenesulfonyloxy); and Hal is defined as chloro, bromo or iodo.

(A) Reacting a compound of formula III wherein $R^{10}$ is carboxy (which compound is hereinafter referred to as "acid of formula III") with a sulfonamide derivative of formula $R^{12}SO_2.NH_2$ in the presence of a dehydrating agent or reacting a reactive derivative of an acid of formula III with a sulfonamide, or a salt thereof, of formula $R^{12}.SO_2.NH_2$.

Thus, for example, a free acid of formula III may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with a sulfonamide of formula $R^{12}.SO_2.NH_2$ in the presence of a suitable solvent or diluent, for example, methylene chloride at a temperature in the range of, for example, 10° to 50° C., but preferably at or near ambient temperature.

Alternatively, a reactive derivative of an acid of formula III, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulfonamide of formula $R^{12}.SO_2.NH_2$, conveniently at or near ambient temperature and in a suitable solvent or diluent, for example, tetrahydrofuran, dimethylformamide or methylene chloride.

An acid of formula III wherein $R^{10}$ is a carboxy group may be obtained by decomposing a suitable ester of formula III in which $R^{10}$ is $COOR^h$ wherein $R^h$ is a conveniently removed acid protecting group (which compound is hereinafter referred to as "ester of formula III"), for example, phenyl, benzyl, or (1–6C)alkyl optionally bearing an acetoxy, (1–4C)alkoxy or (1–4C)alkylthio substituent. A particular value for $R^h$ is, for example, methyl, ethyl, propyl, t-butyl, acetoxymethyl, methoxymethyl, 2-methoxyethyl, methylthiomethyl, phenyl, or benzyl.

The starting acids of formula III wherein $R^{10}$ is carboxy are active as leukotriene antagonists, and they are included within the scope of the invention. In addition, certain of the corresponding esters of formula III wherein $R^{10}=COOR^h$ may be active in their own right as leukotriene antagonists (such as, for example, by in vivo conversion to the corresponding carboxylic acid), for example, those wherein $R^h$ is (1–6C)alkyl, and they are also included within the scope of the invention.

It will be appreciated that the decomposition of an ester of formula III can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when $R^h$ is methyl, the ester may be decomposed by nucleophilic demethylation with, for example, lithium thioethoxide in a solvent such as N,N'-dimethylpropyleneurea. Alternatively, it may in certain circumstances, for example, when $R^h$ is t-butyl, be possible to carry out the decomposition by thermal means, for example, by heating the ester of formula III at a temperature of, for example, 100°–150° C., alone or in a suitable solvent or diluent such as diphenylether. In addition, when $R^h$ is t-butyl, the decomposition may be performed, for example, by using trimethylsilyl triflate and then water, in a conventional manner. Still further, in certain circumstances, for example, when $R^h$ is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15°–100° C. and conveniently at or near ambient temperature. When such a method is employed, the resulting carboxylic acid of formula III, wherein $R^{10}$ is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulfuric acid.

(B) Acylating an amine of formula IV.

A suitable acylating agent when W is oxy or a direct link is, for example, an acid halide of the formula $R^1.Xa.CO$ Hal wherein Xa has one of above-mentioned values for W. A suitable acylating agent when W is imino is, for example, an isocyanate of the formula $R^1.NCO$.

When an acid halide is used as the acylating agent, a suitable base such as triethylamine, N-methylmorpholine, pyridine, 2,6-lutidine or 4-(dimethylamino)pyridine is conveniently also employed, preferably together with a suitable inert solvent or diluent, for example, dichloromethane, tetrahydrofuran or 1,2-dimethoxyethane. The same or similar inert solvents or diluents may be used when an isocyanate or isothiocyanate is employed as the acylating agent.

When W is a direct link, the acylating agent may also be a carboxylic acid of the formula $R^1.CO_2H$. In which case a suitable coupling agent, for example, a carbodiimide (such as dicyclohexylcarbodiimide or 1-(3-dimethylaminopropyl)-3-ethylcarbodiimide, or a salt thereof) or 1,1'-carbonyldiimidazole, is also employed, preferably together with a suitable inert solvent or diluent, for example, one of those mentioned above for use with an acid halide.

In general, the acylations are carried out at a temperature in the range of, for example, −20° to 60° C. and, conveniently, at or near ambient temperature.

(C) Reduction of the double bond of a compound of formula I in which $R^1$, $R^2$ or $R^9$ contains one double bond to provide a corresponding compound of formula I in which $R^1$, $R^2$ or $R^9$ contains no double bond, or reduction of a double bond of a compound corresponding to a compound of formula I, but in which the link corresponding to M contains a double bond, to afford a corresponding compound of formula I.

Preferred reduction conditions include, for example, catalytic hydrogenation over palladium on carbon in a suitable solvent such as methanol, ethanol, ethyl acetate, or tetrahydrofuran at ambient temperature, and, optionally, the addition of an equivalent of a base, such as, for example, potassium hydroxide or triethylamine.

In general, it is preferred to prepare an ester of formula III, decompose the ester of formula III to provide an acid of formula III, and to use procedure (A) as a final step. As a result, procedures corresponding to procedures (B) and (C) may be preferably carried out on esters corresponding to formula IV or esters of formula III.

Pharmaceutically acceptable salts may be obtained using standard procedures well known in the art, for example, by reacting a compound of formula I with a suitable base affording a physiologically acceptable cation.

The necessary starting materials for the above procedures may be made by procedures which are selected from standard techniques of organic chemistry, techniques which are analogous to the synthesis of known, structurally similar compounds, and techniques which are analogous to the above described methods and those described in the Examples.

In general, a preferred method of synthesis involves an ester of formula III as a key intermediate. An ester of formula III may generally be obtained from a corresponding ester of formula V in which $R^c$ is a simple substituent, such as, for example, amino, formyl or iodo. Examples of synthetic routes for this preparation of esters of formula III are outlined in the Schemes.

In Scheme Ia are outlined routes from 7-nitrotetralone to intermediate naphthalene compounds of formula Va, wherein $R^9$ is hydrogen, to corresponding naphthalene starting material esters of formula IIIa, wherein $R^9$ is hydrogen and $R^{10}$ is $COOR^h$. Thus, according to the procedures of Example 1, Example 2 and process (B), 7-nitrotetralone may be converted into an ester of formula IIIa, wherein $R^9$ is hydrogen, $R^{10}$ is $COOR^h$ and A is $R^1.W.CO.NH$- or to an amine of formula Va, wherein $R^c$ is amino and $R^9$ is hydrogen. According to the procedures of Example 2, the amine may be converted into a corresponding aldehyde of formula Va, wherein $R^c$ is formyl and $R^9$ is hydrogen. Further according to the procedures of Example 2, the aldehyde may be converted into a corresponding carboxamide of formula IIIa, wherein $R^9$ is hydrogen, $R^{10}$ is $COOR^h$ and A is $R^2.NH.CO$-. By a standard homologation procedure, the aldehyde may be converted into a corresponding acetic acid derivative of formula Va, wherein $R^c$ is $CH_2COOH$ and $R^9$ is hydrogen and coupled to an amine of formula $R^1R^2NH$ to afford an ester of formula IIIa, wherein $R^9$ is hydrogen, $R^{10}$ is $COOR^h$ and A is $R^1R^2N.CO.CH_2$-. By using analogous procedures to those of Example 3, an aldehyde of formula Va, wherein $R^c$ is formyl and $R^9$ is hydrogen, may be converted into a corresponding ester of formula IIIa wherein $R^9$ is hydrogen, $R^{10}$ is $COOR^h$ and A is $R^1R^2N.CO.CH(CH_3)CH_2$-. By using analogous procedures to those of Example 5, the formyl group may be elaborated to afford a corresponding ester of formula IIIa wherein $R^9$ is hydrogen, $R^{10}$ is $COOR^h$ and A is $R^1R^2N.CO(CH_2)_3$-.

In Scheme Ib are outlined routes from 6-nitroindanone to intermediate indane compounds of formula Vb, wherein $R^9$ is hydrogen, to corresponding indene starting material esters of formula IIIb, wherein $R^9$ is hydrogen and $R^{10}$ is $COOR^h$. Thus, according to the procedures of Example 6, 6-nitro-indane may be converted into an amino indene of formula Vb, wherein $R^c$ is amino and $R^9$ is hydrogen (preferably isolated as its hydrochloride salt), and further converted into an ester of formula IIIb, wherein $R^9$ is hydrogen, $R^{10}$ is $COOR^h$ and A is $R^1.W.CO.NH$-. An amine of formula Vb, wherein $R^c$ is amino and $R^9$ is hydrogen, may be diazotized and treated with potassium iodide to afford a corresponding iodo compound of formula Vb, wherein $R^c$ is iodo and $R^9$ is hydrogen. An iodo compound of formula Vb, wherein $R^c$ is iodo and $R^9$ is hydrogen may be aminocarbonylated using a palladium (0) catalyst and an excess of an amine of formula $R^1NH_2$ to afford a corresponding ester of formula IIIb wherein $R^9$ is hydrogen, $R^{10}$ is $COOR^h$ and A is $R^1.NH.CO$-. (See, R. F. Heck, et al, *J. Org. Chem.* (1974) 39, 3327.) Also, an iodo compound of formula Vb, wherein $R^c$ is iodo and $R^9$ is hydrogen may be coupled with an amide of formulae $R^1R^2N.CO.M.Br$ or $R^1R^2.N.CO.M.I$ using a similar procedure to one known for coupling the corresponding esters with a transition metal catalyst. (Alternatively, an ester may be coupled and converted into an amide.) (For examples of coupling $Br.Zn.CH_2COOC_2H_5$, see J. F. Fauvarque, et al, *J. Organometallic Chem.* (1979) 177, 273. For examples of coupling $I.Zn.(CH_2)_2.COOC_2H_5$ and $I.Zn.(CH_2)_3.COOC_2H_5$, see Z. Yoshida, et al, *Tet. Letters* (1986) No. 27, 955.

A naphthalene ester of formula IIIa, wherein $R^9$ is hydrogen and $R^{10}$ is $COOR^h$ may be converted into a corresponding ester of formula IIIa, wherein $R^9$ is halogeno and $R^{10}$ is $COOR^h$ by treatment with a conventional halogenating agent, for example, chlorine, bromine or iodonium chloride. An ester of formula IIIa wherein $R^9$ is hydrogen and $R^{10}$ is $COOR^h$ may be converted into a corresponding ester of formula IIIa wherein $R^9$ is (1-6C)alkanoyl and $R^{10}$ is $COOR^h$ by a conventional acylation reaction, for example, by using a (1-6C)alkanoyl chloride and aluminum trichloride. An ester of formula IIIa wherein $R^9$ is (1-6C)alkanoyl and $R^{10}$ is $COOR^h$ may be converted into a corresponding ester of formula IIIa wherein $R^9$ is (1-5C)alkoxy by, sequentially, Baeyer-Villiger oxidation (using, for example, m-chloroperoxybenzoic acid), hydrolysis to the naphthol (with, for example, potassium carbonate in aqueous methanol), and alkylation (using, for example, sodium hydride in dimethylformamide and a (1-5C)alkyl halide). The above-mentioned naphthol may be converted into a corresponding triflate and coupled with methylzinc bromide (from methyllithium and zinc bromide) using similar conditions to those described in Example 1.é. to afford a corresponding ester of formula IIIa wherein $R^9$ is methyl and $R^{10}$ is $COOR^h$. An ester of formula IIIa wherein $R^9$ is (1-6C)alkanoyl and $R^{10}$ is $COOR^h$ may be converted into a corresponding ester of formula IIIa wherein $R^9$ is (1-6C)alkyl, for example, by hydrogenolysis of the carbonyl group using palladium on carbon and acetic acid.

An indene ester of formula IIIb wherein $R^9$ is hydrogen and $R^{10}$ is $COOR^h$ may be converted into a corresponding ester of formula IIIb wherein $R^9$ is (1-5C)alkoxy and $R^{10}$ is $COOR^h$ by, first, formation of the 3-hydroxy compound (for example, by formation of the anion with lithium diisopropylamide, then oxidation, see F. A. Davis, et al, *J. Amer. Chem. Soc.* (1979) 101, 1044) and alkylation of the 3-hydroxy group (using, for example, sodium hydride in dimethylformamide and a (1-5C)alkyl halide). The above-mentioned 3-hydroxy compound may be converted into a corresponding 3-acetoxy compound and the resulting allylic acetate treated with a dialkyl copper lithium reagent to afford a corresponding ester of formula IIIb wherein $R^9$ is (1-6C)alkyl and $R^{10}$ is $COOR^h$ (see E. Keinan, et al, *J. Org. Chem.* (1983) 48, 1772 and references cited therein, and see B. Akermark et al, *Organometallics* (1984) 3, 679).

The majority of the starting materials of formula III, IV and V are novel and are provided as further features of the invention based on their utility as chemical intermediates.

As stated previously, the compounds of formula I possess leukotriene antagonist properties. Thus, they antagonise at least one of the actions of one or more of the arachidonic acid metabolites known as leukotrienes, for example, $C_4$, $D_4$, and/or $E_4$, which are known to be powerful spasmogens (particularly in the lung), to increase vascular permeability and to be implicated in the pathogenesis of asthma and inflammation (see J. L. Marx, *Science*, 1982, 215, 1380-1383) as well as of endotoxic shock (see J. A. Cook, et al., *J. Pharmacol. Exp. Ther.*, 1985, 235, 470) and traumatic shock (see C. Denzlinger, et al., Science, 1985, 230, 330). The compounds of formula I are thus useful in treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, and psoriasis, as well as vasospastic cardiovascular disease, and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.*, 1979, 211, 436) and as also described in European Patent Application number 0 179 619 A1.

The selectivity of action of these compounds as leukotriene antagonists as opposed to non-specific smooth muscle depressants may be shown by carrying out the above in vitro procedure using the non-specific spasmogen barium chloride at a concentration of $1.5 \times 10^{-3}$M, again in the presence of indomethacin at $5 \times 10^{-6}$M.

Alternatively, the antagonistic properties of a compound of formula I can be demonstrated in vitro by a receptor-ligand binding assay described by Aharony (*Fed. Proc.* 46: 691, (1987)). According to this procedure, membrane fractions, containing the $LTD_4/E_4$ receptors, are prepared from guinea-pig lung parenchyma and incubated for 30 minutes at 22° C. with 1nM $^3H$-$LTD_4$ in the absence or presence of tested antagonist. Specific binding, determined under conditions that prevent enzymatic metabolism of $^3H$-$LTD_4$, is the net result of total $^3H$-$LTD_4$ binding minus nonspecific binding determined in the presence of 1-2000 fold excess unlabelled LTD. Each assay is done in duplicate and results (Ki values) are typically a mean of several such determinations in individual receptor batches.

The % inhibition by a tested antagonist, relative to control binding (vehicle alone), is expressed as a fraction of log[antagonist] concentration (in molar units) and the half-maximal inhibition ($IC_{50}$) determined by computerized non-linear least-square analysis. The binding constant (Ki) is then calculated from $IC_{50}$ by the Cheng-Prusoff equation:

$$Ki = \frac{IC_{50}}{\left[1 + \frac{[L]}{Kd}\right]}$$

where [L] is $^3H$-$LTD_4$ concentraton and Kd is the affinity constant of $LTD_4$ to this receptor, determined separately for each batch. (*Biochem. Pharmacol.* 22: 3099-3108, 1973).

In general, the compounds of formula I tested demonstrated statistically significant activity as $LTC_4$, $LTD_4$ and/or $LTE_4$ antagonists in one of the above tests at a concentration of about $10^{-6}$M or much less. For example, a pKi value of 8.5 was determined for the compound of Example 10.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene $LTD_4$ (starting with 2 ml of a 30 microgram/ml solution) and the effect of the test compound on the average time of leukotriene initiated change in breathing pattern (such as onset of dyspnea) recorded and compared with that in undosed, control guinea-pigs. In general, compounds of formula I tested produced a signigicant increase in the time of onset of leukotriene initiated breathing changes following either oral or intravenous administration or by inhalation at a dose of about 100 mg/kg, or much less, without any indication of untoward side-effects at several multiples of the minimum effective dose.

The invention will now be illustrated by the following non-limiting examples in which, unless stated otherwise:

(i) temperatures are given in degrees Celsius (°C.); operations were carried out at room or ambient temperature, that is, at a temperature in the range of 18°-25° C.; air or moisture sensitive reactions were performed under an argon or nitrogen atmosphere;

(ii) evaporation of solvent was carried out using a rotary evaporator under reduced pressure (600-4000 pascals; 4.5-30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, DE, USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz, 250 MHz, 300 MHz or 400 MHz using CDCl₃, DMSO-d₆ or CD₃OD as solvent; conventional abbreviations for signal shape are used, for example: s, singlet; d, doublet; m, multiplet; br, broad; etc.; in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used: v (volume), w (weight); mp (melting point), l [liter(s)], ml (milliliters), g [gram(s)], mg [milligram(s)], min (minutes), h (hour);

(xi) solvent ratios are given in volume: volume (v/v) terms; and (xii) mass spectra (MS) were run with an electron energy of 70 electron volts in the chemical ionization (CI) mode or electron impact (EI) mode; generally only the peak attributable to the parent ion is reported.

EXAMPLE 1

4-[7-(Cyclopentylacetamido)naphth-1-ylmethyl]-3-methoxy-N-(2-methylphenylsulfonyl)benzamide a. 7-Amino-1-tetralone

A mixture of platinum oxide (1.6 g), 0.1M aqueous ferric chloride (1 ml), 7-nitro-1-tetralone (15.8 g) and ethyl acetate (400 ml) in a hydrogenation bottle was hydrogenated at 3.5 bar for 3 h. The catalyst was removed by filtration through diatomaceous earth with methanol wash and the filtrate was evaporated to give crude 7-amino-1-tetralone (13.2 g, 100%) as a brown solid; NMR (80 MHz, DMSO-$d_6$) 1.76–2.17(m, 2H, $CH_2$), 2.34–2.90(m, 4H, $2 \times CH_2$), 5.10 (br s, 2H, $NH_2$), 6.76(dd, 1H, J=8.3, 2.8 Hz), 7.0(d, 1H, J=8.3 Hz), 7.07 (d, 1H, J=2.8 Hz).

b. 7-Cyclopentylacetamido-1-tetralone

To a mixture of 7-amino-1-tetralone (13.2 g) (prepared as described above and used without further purification) and pyridine (8.4 ml) in methylene chloride (130 ml) at 0° C. was added a solution of cyclopentylacetyl chloride (13.2 g) in methylene chloride (20 ml). The reaction was stirred for 30 min and at room temperature for 1.5 h. The mixture was evaporated and the residue was diluted with ethyl acetate, washed (saturated sodium bicarbonate, 1N HCl, brine), dried ($MgSO_4$) and evaporated. The residue was flash chromatographed, eluting with ethyl acetate:methylene chloride (5:95, 7.5:92.5, and 1:9, successively), to give 7-cyclopentylacetamido-1-tetralone (16.6 g, 74%) as a colorless solid; mp 117.0°–118.0° C.

Analysis for $C_{17}H_{21}NO_2$: Calculated: C, 75.25; H, 7.80; N, 5.16. Found: C, 75.11; H, 7.80; N, 5.56.

c. 2-Bromo-7-cyclopentylacetamido-1-tetralone

To a mixture of 7-cyclopentylacetamido-1-tetralone (1.02 g) in ethereal HCl (0.2 ml) and methylene chloride (20 ml) was added a solution of bromine (0.19 ml) in a mixture of ethereal HCl (10 drops) and carbon tetrachloride (1 ml). The reaction was stirred for 3 h and ethyl acetate (60 ml) was added. The mixture was washed (saturated sodium bicarbonate, water, brine), dried ($MgSO_4$), and evaporated. The residue was recrystallized from methylene chloride and petroleum ether to give 2-bromo-7-cyclopentylacetamido-1-tetralone (1.23 g, 95%) as a colorless solid; mp 162.5°–164.0° C.

Analysis for $C_{17}H_{20}BrNO_2$: Calculated: C, 58.29; H, 5.75; N, 3.99. Found: C, 58.00; H, 5.69; N, 3.82.

d. 7-Cyclopentylacetamido-1-naphthol

A mixture of 2-bromo-7-cyclopentylacetamido-1-tetralone (1.1 g) and collidine (12 ml) was heated at 160° C. for 2 h. After cooling, the reaction mixture was diluted with 1:9 tetrahydrofuran:ethyl acetate, washed (1N HCl (4 times), brine), dried ($MgSO_4$) and evaporated to give 7-cyclopentylacetamido-1-napthol (quantitative) as a brown glassy solid which was used without further purification.

An analytical sample of the naphtol was obtained by flash chromatography, eluting with triethyl amine:ethyl acetate:methylene chloride (0:0:1, 0.5:2:97.5 and 1:4:95, successively) and recrystallization from a mixture of ethyl acetate, ether and petroleum ether to give 7-cyclopentylacetamido-1-naphthol; mp 162.0°–165.0° C.

Analysis for $C_{17}H_{19}NO_2 \cdot 0.25 H_2O$: Calculated: C, 74.56: H, 7.18; N, 5.11. Found: C, 74.60; H, 7.05; N, 5.41.

e. 7-(Cyclopentylacetamido)naphth-1-yl triflate

To a mixture of 7-cyclopentylacetamido-1-naphthol (approximately 845 mg) prepared as described above and used without further purification) and pyridine (10 ml) at 0° C. was added triflic anhydride (0.56 ml). After stirring for 15 minutes, the mixture was warmed to room temperature for 1 h and 100 ml of ethyl acetate was added. The mixture was washed (1N HCl (4 times), 0.5N sodium bicarbonate, water, brine), dried ($MgSO_4$), and evaporated. The residue was flash chromatographed, eluting with ethyl acetate:petroleum ether (1:9, 2:8, successively), to give 7-(cyclopentylacetamido)naphth-1-yl triflate (847 mg, 67%) as a yellow solid; mp 111°–116° C.

f. Methyl 4-[7-(cyclopentylacetamido)naphth-1-ylmethyl]-3-methoxybenzoate

A mixture of activated zinc dust (806 mg), methyl 4-bromomethyl-3-methoxybenzoate (2.14 g) and tetrahydrofuran (15 ml) was stirred for 18 h. To the reaction was added dichloro[1,1'-bis(diphenylphosphino)ferrocene]palladium(II) (76 mg). After stirring for 15 min, 7-(cyclopentylacetamido)naphth-1-yl triflate (830 mg) in tetrahydrofuran (10 ml) was added and the mixture was stirred for 72 h. The mixture was added to 100 ml of ethyl acetate and the ethyl acetate solution was washed (1N HCl, brine), dried ($MgSO_4$) and evaporated. The residue was flash chromatographed, eluting with ether:petroleum ether (2:8,4:6, and 1:4, successively), to give a white solid. Recrystallization from methylene chloride and petroleum ether gave the title compound as a colorless solid (705 mg, 79%); mp 172.5°–174.5° C.

Analysis for $C_{27}H_{29}NO_4$: Calculated: C, 75.15; H, 6.77; N, 3.24. Found: C, 74.82; H, 6.78; N, 2.85.

g. 4-[7-(Cyclopentylacetamido)naphth-1-ylmethyl]-3-methoxybenzoic acid

To a mixture of methyl 4-[7-(cyclopentyl acetamido)-naphth-1-ylmethyl]-3-methoxybenzoate (660 mg), methanol (23 ml) and tetrahydrofuran (23 ml) was added a solution of lithium hydroxide monohydrate (321 mg) in water (7.7 ml). Nitrogen was bubbled through the mixture for 30 seconds before it was stoppered and stirred for 72 h. The reaction mixture was evaporated and the residue taken up in 75 ml of 1:9 tetrahydrofuran:ethyl acetate and acidified with 3 ml of 6N HCl. The organic layer was washed (water, brine), dried ($MgSO_4$) and evaporated. Recrystallization of the resulting solid from 1:9 methanol:methylene chloride and petroleum ether gave the title compound as a colorless solid (517 mg, 81%); mp 248.0°–250.0° C.

Analysis for $C_{26}H_{27}NO_4$: Calculated: C, 74.79; H, 6.52; N, 3.35. Found: C, 74.36; H, 6.55; N, 3.26.

h. 4-[7-(Cyclopentylacetamido)naphth-1-ylmethyl]-3-methoxy-N-(2-methylphenylsulfonyl)benzamide To a mixture of 4-[7-(cyclopentylacetamido)naphth-1-ylmethyl]-3-methoxybenzoic acid (375 mg), 2-methylbenzenesulfonamide (231 mg), and 1-(3-dimethylaminopropyl)-3-ethylcarbodiimide hydrochloride (259 mg) in methylene chloride (9 ml) was added 4- dimethylamino pyridine (165 mg); and the mixture was stirred for 24 h. The mixture was added to 60 ml of 1:9 tetrahydrofuran:ethyl acetate: and the organic solution was washed (1N HCl, water, brine), dried (MgSO$_4$), and evaporated. The residue was purified by flash chromatorgraphy, eluting methylene chloride:acetone:-methanol (90:8:0, 90:8:1, 90:8:2 successively). The crude product was recrystallized from 2:8 methanol:methylene chloride and petroleum ether to give the title compound as a colorless solid (263 mg, 51%); mp 248.0°–249.0° C.

Analysis for $C_{33}H_{34}N_2O_5S \cdot 0.5\ H_2O$: Calculated: C, 68.37; H, 6.08: N, 4.83. Found: C, 68.25; H, 6.22; N, 4.80.

EXAMPLE 2

4-[7-(2-Ethylbutylcarbamoyl)naphth-1-ylmethyl]-3-methoxy-N-(2-methylphenylsulfonyl)benzamide a. Methyl 4-(7-aminonaphth-1-ylmethyl)-3-methoxybenzoate

A mixture of methyl 4-[7-(cyclopentylacetamido)-naphth-1-ylmethyl]-3-methoxybenzoate (15.00 g), anhydrous p-toluenesulfonic acid (11.97 g), and methanol (dried over 3A molecular sieves) (70 ml) was refluxed for 42 hours. After cooling, the mixture was added to ethyl acetate (250 ml), washed (saturated sodium bicarbonate, brine), dried (MgSO$_4$) and evaporated. The solid obtained was recrystallized from 1:12 methanol:-methylene chloride and petroleum ether to give methyl 4-(7-aminonaphth-1-ylmethyl)-3-methoxybenzoate (10.15 g, 91%) as a light tan solid; mp 138°–40° C., MS(CI), m/e=322(M+H).

b. 1-(4-Methoxycarbonyl-2-methoxyphenylmethyl)naphthalene-7-diazonium tetrafluoroborate To a mixture of boron trifluoride etherate (1.85 ml), and chloroform (29 ml, Al$_2$O$_3$ treated) at 5° C. was added a solution of methyl 4-(7-aminonaphth-1-ylmethyl)-3-methoxybenzoate (2.42 g) in tetrahydrofuran (10 ml) and the mixture stirred for 15 min. To the resulting suspension was quickly added t-butyl nitrite (0.98 ml), in a single portion. The reaction was allowed to warm to 10° C in 30 min and stirred for 3 h. The mixture was filtered with ether wash to afford 1-(4-methoxycarbonyl-2-methoxyphenylmethyl)-naphthalene-7-diazonium tetrafluoroborate (2.63 g, 83%) as a yellow solid; mp 180° C. (d).

c. Methyl 4-(7-cyanonaphth-1-ylmethyl)-3-methoxybenzoate

A mixture of cuprous cyanide (2.52 g), sodium cyanide (1.68 g), and dimethylformamide (50 ml, distilled over CaH$_2$) was stirred for 1 h. The homogeneous solution was cooled to 0° C. and a solution of 1-(4-methoxycarbonyl-2-methoxyphenylmethyl)naphthalene-7-diazonium tetrafluoroborate (2.62 g), in dimethylformamide (12 ml, distilled over CaH$_2$) was added. The reaction was stirred for 15 min at 0° C. and then at room temperature for 16 h. The mixture was added to ethyl acetate (200 ml) and water (300 ml) and filtered through diatomaceous earth with ethyl acetate washes. The organic layer was washed (water, brine), dried (MgSO$_4$), and evaporated. Flash chromatography of the residue, eluting with methylene chloride, and trituration of the product with hot ether afforded methyl 4-(7-cyanonaphth-1-ylmethyl)-3-methoxybenzoate (1.04 g, 56%) as a pale yellow solid; mp 138.5°–139.5° C.; MS(CI), m/e=33Z(M+H).

d. Methyl 4-(7-formylnaphth-1-ylmethyl)-3-methoxybenzoate

To a mixture of methyl 4-(7-cyanonaphth-1-ylmethyl)-3-methoxybenzoate (1.06 g), sodium hypophosphite hydrate (2.25 g), glacial acetic acid (4 ml), pyridine (8 ml) and water (4 ml) was added Raney nickel (330 mg of material resulting from decanting water from a 50% (w/w) slurry in water). The reaction mixture was heated to 50° C. for 1 h and cooled, ethyl acetate was added and the mixture filtered through diatomaceous earth with ethyl acetate wash. The organic layer was washed (1N HCl twice, brine), dried (MgSO$_4$) and evaporated. Purification by flash chromatography, eluting with methylene chloride, and trituration with ether afforded methyl 4-(7-formylnaphth-1-ylmeth-yl)-3-methoxybenzoate (506 mg, 47%) as a colorless solid; mp 103°–4° C., MS(CI), m/e=336(M+H).

e. Methyl 4-(7-carboxynaphth-1-ylmethyl)-3-methoxybenzoate

A solution of Jones reagent (1.53 ml) [prepared from 26.72 g chromium trioxide in 23 ml concentrated sulfuric acid, diluted with water to 100 ml] was added to a solution of methyl 4-(7-formylnaphth-1-yl-methyl)-3-methoxybenzoate (409 mg) in dimethylformamide (12 ml, distilled over CaH$_2$). The mixture was stirred for 1 h and was partitioned between methylene chloride and 1N HCl. The organic layer was washed (1N HCl (twice), brine), dried (MgSO$_4$) and evaporated. The residue was triturated with ether, ground to a powder and vacuum dried at 120° C. for 12 h to afford methyl 4-(7-carboxynaphth-1-ylmethyl)-3-methoxybenzoate (347 mg, 81%) as a pale yellow solid; mp 229.0°–230° C.; MS(CI), m/e=351(M+H).

f. Methyl 4-[7-(2-ethylbutylcarbamoyl)naphth-1-ylmethyl]-3-methoxybenzoate

A mixture of methyl 4-(7-carboxynaphth-1-ylmethyl)-3-methoxybenzoate (342 mg), 4-dimethylaminopyridine (358 mg), 1-(3-dimethylaminopropyl)-3-ethylcarbodiimide hydrochloride (560 mg), and 2-ethylbutylamine (198 mg), was dissolved in 3:1 methylene chloride:dimethylformamide (distilled over CaH$_2$) (4 ml) and stirred for 18 h. Methylene chloride was added and the solution was washed (1N hydrochloric acid, brine), dried (MgSO$_4$) and evaporated to give a yellow foam. Recrystallization from 1:2 methylene chloride:hexane (30 ml) gave methyl 4-[7-(2-ethylbutyl-carbamoyl)naphth-1-ylmethyl]-3-methoxybenzoate (326 mg, 77%) as a colorless solid; mp 129.5°–130.5° C.

Analysis for $C_{27}H_{31}NO_4$: Calculated: C, 74.80; H, 7.21; N, 3.23. Found: C, 74.43; H, 7.19; N, 3.44.

g. 4-[7-(2-Ethylbutylcarbamoyl)naphth-1-ylmethyl]-3-methoxybenzoic acid

A solution of lithium hydroxide monohydrate (150 mg) in water (4 ml) was added to a solution of methyl 4-(7-(2-ethylbutylcarbamoyl)naphth-1-ylmethyl)-3-methoxybenzoate (310 mg) in 1:1 methanol:tetrahydrofuran (15 ml). The mixture was stirred for 18 h. After most of the solvent was evaporated, water (7 ml) was added. The mixture was acidified with 1N hydrochloric acid and the precipitate was filtered, triturated with 25 ml of 10:1 ether:methanol, ground to a powder and vacuum dried at 100° C for 12 h to give 4-[7-(2-ethylbutylcarbamoyl)naphth-1-ylmethyl]-3-methoxybenzoic acid (221 mg, 74%) as a colorless solid; mp 198.0°-199.0° C.

Analysis for $C_{26}H_{29}NO_4 \cdot 0.25\ H_2O$: Calculated: C, 73.65; H, 7.01; N, 3.30. Found: C, 73.76; H, 7.00; N, 3.24.

h. 4-[7-(2-Ethylbutylcarbamoyl)naphth-1-ylmethyl]-3-methoxy-N-(2-methylphenylsulfonyl)benzamide A mixture of 4-[7-(2-ethylbutylcarbamoyl)naphth-1-ylmethyl]-3-methoxybenzoic acid (189 mg), 4-dimethylaminopyridine (110 mg), 1-(3-dimethylaminopropyl)-3-ethylcarbodiimide hydrochloride (172 mg), and o-toluenesulfonamide (96 mg) in methylene chloride (2 ml) was stirred for 18 h. Methylene chloride (25 ml) was added, and the solution was washed (1N hydrochloric acid, brine), dried (MgSO$_4$) and evaporated. The residue was recrystallized from 21 ml of 1:0.5:1 methylene chloride:methanol:hexane, ground to a powder and vacuum dried at 100° C. to give the title compound (179 mg, 70%) as a colorless solid; mp 126.0°-128.0° C.

Analysis for $C_{33}H_{36}N_2O_5 \cdot 0.25\ H_2O$: Calculated: C, 68.67; H, 6.37; N, 4.85. Found: C, 68.37; H, 6.31: N, 4.84.

EXAMPLE 3

3-Methoxy-N-(2-methylphenylsulfonyl)-4-[7-[2-(propylcarbamoyl)propyl]naphth-1-ylmethyl]benzamide a. Methyl E-4-[7-[2-(t-butoxycarbonyl)prop-1-enyl]naphth-1-ylmethyl]-3-methoxybenzoate A mixture of t-butyl 2-(triphenylphosphoranylidene)-propionate (9.37 g) and methyl 4-(7-formylnaphth-1-ylmethyl)-3-methoxybenzoate (4.01 g) in dry dioxane (100 ml) was refluxed for 4 hours. The solvent was evaporated and the residue was flash chromatographed, eluting with 15:85 ethyl acetate:petroleum ether to give methyl E-4-[7-[2-(t-butoxycarbonyl)prop-1-enyl]-naphth-1-ylmethyl]-3-methoxybenzoate (6.43 g, quantitative yield) as a thick amber oil; MS(EI), m/e=446(M+.). This material was used without further purification.

b. Methyl E-4-[7-(2-carboxyprop-1-enyl)naphth-1-ylmethyl]-3-methoxybenzoate Trifluoroacetic acid (25 ml) was added to a 0° C. solution of methyl E-4-[7-[2-(t-butoxycarbonyl)prop-1-enyl]naphth-1-ylmethyl]-3-methoxybenzoate (6.43 g) in methylene chloride (50 ml). After stirring for 4 hours, the solvent was evaporated without heating. The residue was triturated with ether and the colorless solid filtered. The filtrate was concentrated and hexane was added to give another crop of product as a pale yellow solid. The two crops were combined and dried to give methyl E-4-[7-(2-carboxyprop-1-enyl)naphth-1-ylmethyl]-3-methoxybenzoate (4.43 g, 94%); mp 187.0°-187.5° C.; MS(EI), m/e=390(M+.).

c. Methyl 4-[7-(2-carboxypropyl)naphth-1-ylmeth-yl]-3-methoxybenzoate

A mixture of 10% (w/w) palladium on carbon (0.75 g) and methyl E-4-[7-(2-carboxyprop-1-enyl)naphth-1-ylmethyl]-3-methoxybenzoate (4.38 g), in tetrahydrofuran (100 ml) was hydrogenated under 3.7 bar of hydrogen for 2 h. To the reaction mixture was added a slurry of 10% (w/w) palladium on carbon (0.75 g) and tetrahydrofuran (20 ml). After hydrogenating for 2 h more, the reaction mixture was filtered through diatomaceous earth with tetrahydrofuran washes. The solvent was evaporated and the residue was dissolved in ether. Evaporation and vacuum drying overnight afforded methyl 4-[7-(2-carboxypropyl)naphth-1-ylmethyl]-3-methoxybenzoate (4.22 g, 96%) as a colorless glassy solid; mp 110.0°-129.0° C.; MS(CI), m/e=393(M+H).

d. Methyl 4-[7-[2-(propylcarbamoyl)propyl]naphth-1-ylmethyl]-3-methoxybenzoate A mixture of methyl 4-[7-(2-carboxypropyl)naphth-1-ylmethyl]-3-methoxybenzoate (1.176 g), 4-dimethylaminopyridine (440 mg), 1-(3-dimethylaminopropyl)-3-ethylcarbodiimide hydrochloride (690 mg), propylamine (0.295 ml) and methylene chloride (20 ml) was stirred for 18 h. Ethyl acetate (100 ml) was added, the solution was washed (1N hydrochloric acid, brine) and dried (MgSO$_4$). Evaporation and flash chromatography, eluting with 2:30:70 triethylamine:ethyl acetate:-petroleum ether, gave a solid. Recrystallization from methylene chloride and hexane, followed by grinding to a powder and vacuum drying, afforded methyl 4-[7-[2-(propylcarbamoyl)propyl]naphth-1-ylmethyl]-3-methoxybenzoate (910 mg, 70%) as a colorless solid; mp 129.5°-130.0° C.; MS(CI), m/e=434(M+H).

e. 4-[7-[2-(Propylcarbamoyl)propyl]naphth-1-ylmethyl]-3-methoxybenzoic acid Using a similar procedure to that described in Example 2.g., except starting from methyl 4-[7-[2-(propylcarbamoyl)propyl]naphth-1-ylmethyl]-3-methoxybenzoate, the acid was obtained (87%) as a colorless solid; mp 199.0°-200.5° C.; MS(CI), m/e=420(M+H).

f. 3-Methoxy-N-(2-methylphenylsulfonyl)-4-[7-[2-(propylcarbamoyl)propyl]naphth-1-ylmethyl]benzamide Using a similar procedure to that described in Example 2.h., except starting from 4-[7-[2-(propylcarbamoyl)propyl]naphth-1-ylmethyl]-3-methoxybenzoic acid, the title compound was obtained (88%) as a colorless solid; mp 210.0°-212.0° C., MS(CI), m/e=573(M+H).

g. t-Butyl 2-(triphenylphosphoranylidene)propionate

The ylide used in part a., above, was prepared as follows: Triphenylphosphine (33 g), t-butyl 2-bromopropionate (22 g) and triethylamine (12.7 g) were dissolved in ethyl acetate (150 ml) and refluxed for 48 h. Methylene chloride (300 ml) was added to the cooled solution; the mixture was washed (10% w/w aqueous sodium hydroxide, water, brine), dried (MgSO$_4$) and evaporated. The residual oil was triturated with hexane to give t-butyl 2-(triphenylphoranylidene)-propionate (33 g, 67%) as a yellow powder; mp 144°-151° C.; partial NMR (250 MHz, CDCl$_3$): 1.0(br signal, 9H, t-butyl), 1.55(d, J=14.4 Hz, 3H, CH$_3$), 7.3-7.9(complex m, 15H, Ar$\underline{H}$).

EXAMPLE 4

3-Methoxy-N-(phenylsulfonyl)-4-[7-[2-(propylcarbamoyl)propyl]naphth-1-ylmethyl]benzamide Using a similar procedure to that described in Example 2.h., except starting from 4-[7-[2-(propylcarbamoyl)propyl]naphth-1-ylmethyl]-3-methoxybenzoic acid and benzenesulfonamide, the title compound was obtained (83%) as a colorless solid; mp 214.0°–217.5° C., MS(CI), m/e=559(M+H).

EXAMPLE 5

4-[7-(3-Dimethylcarbamoylpropyl)naphth-1-ylmethyl]-3-methoxy-N-(2-methylphenylsulfonyl)benzamide a. Methyl 4-[7-(3-carboxy-2,3,4,5-tetrahydro-5-oxofuran-2-yl)naphth-1-ylmethyl]-3-methoxybenzoate Triethylamine (4.54 g) was added to a mixture of methyl 4-[7-formylnaphth-1-ylmethyl]-3-methoxybenzoate (5.00 g), succinic anhydride (2.99 g), zinc chloride (6.11 g) and methylene chloride (50 ml). During the addition, the reaction was cooled with an ambient temperature bath. The mixture was stirred for 18 h and poured into a vigorously stirred solution of 1:1 ethyl acetate:2N hydrochloric acid (500 ml). The organic layer was washed (water, brine) and dried (MgSO$_4$). After the evaporation of solvent and dissolving the residue in saturated sodium bicarbonate, the solution was washed with ether. The aqueous solution was neutralized with 6N hydrochloric acid, acidified to pH 2 with 1N hydrochloric acid and extracted with ethyl acetate. The organic layer was washed (water, brine), dried (MgSO$_4$) and evaporated to give methyl 4-[7-(3-carboxy-2,3,4,5-tetrahydro-5-oxofuran-2-yl)naphth-1-ylmethyl]-3-methoxybenzoate (6.16 g, 95%, as a mixture of diastereomers) as a pale yellow foam; MS(CI), m/e=434(M+H).

b. Methyl E-4-[7-(3-carboxyprop-1-enyl)naphth-1-ylmethyl]-3-methoxybenzoate Methyl 4-[7-(3-carboxy-2,3,4,5-tetrahydro-5-oxofuran-2-yl)naphth-1-ylmethyl]-3-methoxybenzoate (2.80 g) was heated at 210°, under an argon atmosphere, for 15 h to give a mixture of methyl E-4-[7-(3-carboxyprop-1-enyl)naphth-1-ylmethyl]-3-methoxybenzoate and methyl 4-[7-(2,3,4,5-tetrahydro-5-oxofuran-2-yl)naphth-1-ylmethyl]-3-methoxybenzoate (2.52 g, 100%) as a glassy solid; MS(CI), m/e=390 (M+H).

c. Methyl 4-[7-(3-carboxypropyl)naphth-1-ylmethyl]-3-methoxybenzoate

A mixture of methyl E-4-[7-(3-carboxyprop-1-enyl)-naphth-1-ylmethyl]-3-methoxybenzoate and methyl 4-[7-(2,3,4,5-tetrahydro-5-oxofuran-2-yl)naphth-1-ylmethyl]-3-methoxybenzoate (2.52 g), ethyl acetate (70 ml) and 10% (w/w) palladium on carbon (0.25 g) was hydrogenated under atmospheric pressure for 18 h. The reaction mixture was filtered through diatomaceous earth with ethyl acetate wash. The filtrate was evaporated to give methyl 4-[7-(3-carboxypropyl)naphth-1-ylmethyl]-3-methoxybenzoate (2.42 g, 96%) as a yellow foam; MS(CI), m/e=392(M+H).

d. Methyl 4-[7-(3-dimethylcarbamoylpropyl)naphth-1-ylmethyl]-3-methoxybenzoate To a mixture of methyl 4-[7-(3-carboxypropyl)-naphth-1-ylmethyl]-3-methoxybenzoate (2.40 g), tetrahydrofuran (70 ml) and triethylamine (0.681 g) was added isobutyl chloroformate (0.87 ml) After stirring for 30 min, dimethylamine (2.0 g) was bubbled into the solution and stirring continued for 18 h. The reaction mixture was partitioned between ethyl acetate and 1N hydrochloric acid. The organic layer was washed (1N hydrochloric acid, aqueous sodium bicarbonate (5% w/w), brine) and dried (MgSO$_4$). Evaporation and flash chromatography, eluting with ethyl acetate:methylene chloride (0:1, 1:10 and 2:10, successively), to give methyl 4-[7-(3-dimethylcarbamoylpropyl)naphth-1-ylmethyl]-3-methoxybenzoate (1.10 g, 43%) as a glassy solid; MS(CI), m/e=419(M+H).

e. 4-[7-(3-Dimethylcarbamoylpropyl)naphth-1-ylmethyl]-3-methoxybenzoic acid Using a similar procedure to that described in Example 2.g., except starting from methyl 4-[7-(3-dimethylcarbamoylpropyl)naphth-1-ylmethyl]-3-methoxybenzoate, the acid was obtained (89%) as a light tan powder; mp 231.0°–232.0° C.; MS(CI), m/e=405(M+H).

f. 4-[7-(3-Dimethylcarbamoylpropyl)naphth-1-ylmethyl]-3-methoxy-N-(2-methylphenylsulfonyl)benzamide Using a similar procedure to that described in Example 2.h.,except starting from 4-[7-(3-dimethylcarbamoylpropyl)naphth-1-ylmethyl]-3-methoxybenzoic acid, the title compound was obtained (65%) as a light tan powder; mp 166.0°–168° C.

Analysis for C$_{32}$H$_{32}$N$_2$O$_5$S.0.25 H$_2$O: Calculated: C, 68.24; H, 6.17; N, 4.97. Found C, 68.23; H, 6.11; N, 4.78.

EXAMPLE 6

4-[6-(Cyclopentylacetamido-3H-inden-1-ylmethyl]-3-methoxy-N-(2-methylphenylsulfonyl)benzamide a. 6-(Trifluoroacetamido)indan-1-one

Using a similar procedure to that described for Example 1.a., except starting with 6-nitro-indanone (C. K. Ingold and H. A. Piggott, *J. Chem. Soc.*, (1923) 123, 1469) and trifluoroacetic anhydride, 6-(trifluoroacetamido)indan-1-one was obtained (73%); mp 172.5°–173.5° C.

b. 1-Hydroxy-6-(trifluoroacetamido)indane

A mixture of 10% (w/w) palladium on carbon (2.34 g), 6-(trifluoroacetamido)indan-1-one (7.79 g), ethyl acetate (53 ml) and dimethylformamide (11 ml) was hydrogenated at atmospheric pressure for 72 h. The reaction mixture was filtered through diatomaceous earth with ethyl acetate wash and evaporated. The residue was flash chromatographed, eluting with 95:5 methylene chloride:methanol, and triturated with ether to give 1-hydroxy-6-(trifluoroacetamido)indane (4.41 g, 56%) as a colorless solid; mp 123.0°–124.5° C.; MS(EI), m/e=245(M+.).

c. 6-(Trifluoroacetamido)-3H-indene

To a mixture of 1-hydroxy-6-(trifluoroacetamido)indane (4.37 g), triphenylphosphine (7.01 g), methylene chloride (70 ml) and tetrahydrofuran (7 ml), at 0° C., was added carbon tetrabromide (8.87 g) in four portions. After 15 min, the reaction mixture was allowed to warm to room temperature and stirred for 4 h. Ethyl acetate was added and the solution was washed (water, brine), dried (MgSO$_4$) and evaporated. The residue was flashed chromatographed, eluting with methylene chloride, to give 6-(trifluoroacetamido)-3H-indene (3.09 g, 76%) as a colorless solid; mp 131.5°–132.5° C.; MS(CI), m/e=228(M+H).

d. Methyl 4-methoxy-4-[6-(trifluoroacetamido)-3H-inden-1-ylmethyl]-3-methoxybenzoate A solution of n-butyllithium in hexane (1.4M, 38.82 ml) was added to a −78° C. solution of diisopropylamine (7.85 ml) in tetrahydrofuran (25 ml). After stirring for 15 min, a solution of 6-(trifluoroacetamido)-3H-indene (5.92 g) in tetrahydrofuran (25 ml) was added and stirred for 1 h. The reaction mixture was cooled to −100° C. and a solution of methyl 4-bromomethyl-3-methoxybenzoate (8.44 g) in tetrahydrofuran (35 ml) was added. The mixture was allowed to warm to room temperature and stirred for 18 h. The reaction mixture was added to saturated ammonium chloride (100 ml) and ethyl acetate (150 ml). The mixture was washed (water, brine), dried (MgSO$_4$) and evaporated. The residue was recrystallized from 10:1 methylene chloride:hexane to give methyl 3-methoxy-4-[6-(trifluoroacetamido)-3H-inden-1-ylmethyl]benzoate (1.48 g, 14%). The residue derived from the filtrate was recrystallized from 3:1 methylene chloride:hexane to give a mixture of methyl 3-methoxy-4-[6-(trifluoroacetamido)-3H-inden-1-ylmethyl]benzoate and methyl 3-methoxy-4-[6-(trifluoroacetamido)-1H-inden-1-ylmethyl]benzoate (1.92 g). This mixture was treated with 1,8-diazabicyclo[5.4.0]undec-7-ene (1.11 g) and tetrahydrofuran (20 ml) for 18 h. After partitioning between ethyl acetate (85 ml) and 1N hydrochloric acid, the organic layer was washed (brine) and dried (MgSO$_4$). Evaporation and trituration with methylene chloride gave a colorless solid. This was combined with the above material to give methyl 3-methoxy-4-[6-(trifluoroacetamido)-3H-inden-1-ylmethyl]-3-methoxybenzoate (2.81 g, 27% total yield from 6-(trifluoroacetamido)-3H-indene); mp 198.5°–200.0° C.; MS(CI), m/e=406(M+H).

e. Methyl 4-(6-amino-3H-inden-1-ylmethyl)-3-methoxybenzoate hydrochloride

Sodium borohydride (0.24 g), was added to a 0° C. mixture of methyl 3-methoxy-4-[6-(trifluoroacetamido)-1H-inden-1-ylmethyl]benzoate (1.25 g), tetrahydrofuran (14 ml) and methanol (2 ml). After 15 min, the reaction was stirred at room temperature for 2 h and cooled to 0° C. 1N Hydrochloric acid was added and the mixture was extracted with ethyl acetate. The organic layer was washed (sodium bicarbonate, water, brine) and dried (MgSO$_4$). Evaporation, dissolution in ether (50 ml) and addition of ethereal hydrogen chloride (5 ml) afforded methyl 4-(6-amino-3H-inden-1-ylmethyl)-3-methyoxybenzoate hydrochloride (0.85 g, 79%) as a colorless solid; mp 213.0°–215.0° C.; MS(CI), m/e=310 (M+H).

f. Methyl 4-[6-(cyclopentylacetamido)-3H-inden-1-ylmethyl]-3-methoxybenzoate Using a similar procedure to that described in Example 1.b., except starting from methyl 4-(6-amino- 3H-inden-1-ylmethyl)-3-methoxybenzoate hydrochloride with excess pyridine, in methylene chloride and dimethylformamide, methyl 4-[6-(cyclopentylacetamido)-3H-inden-1-ylmethyl]-3-methoxybenzoate was obtained (79%) as a colorless solid; mp 178.0°–179.0° C.

g. 4-[6-(Cyclopentylacetamido)-3H-inden-1-yl-methyl]-3-methoxybenzoic acid

Using a similar procedure to that described in Example 2.g., except starting from methyl 4-[6-(cyclopentylacetamido)-3H-inden-1-ylmethyl]-3-methoxybenzoate, the acid was obtained (77%) as a colorless solid; mp 222.0°–223.5° C.; MS(CI), m/e=406(M+H).

Analysis for C$_{25}$H$_{27}$NO$_4$.0.25 H$_2$O: Calculated: C, 73.24; H, 6.76; N, 3.42. Found: C, 73.37; H, 6.74; N, 3.39.

h. 4-[6-(Cyclopentylacetamido-3H-inden-1-ylmeth-yl]-3-methoxy-N-(2-methylphenylsulfonyl)benzamide Using a similar procedure to that described in Example 2.h., except starting from 4-[6-(cyclopentylacetamido)-3H-inden-1-ylmethyl]-3-methoxybenzoic acid, the title compound was obtained (49%) as a colorless solid; mp 227.0°–228.0° C.; MS(CI), m/e=539(M+H).

Analysis for C$_{32}$H$_{34}$N$_2$O$_5$S.0.25 H$_2$O: Calculated: C, 68.24; H, 6.17; N, 4.97. Found: C, 68.11; H, 6.13; N, 4.96.

EXAMPLE 7

3-Methoxy-N-(2-methylphenylsulfonyl)-4-[7-(4-morpholino-4-oxobutyl)naphth-1-ylmethyl]benzamide a. Methyl 3-methoxy-4-[7-(4-morpholino-4-oxobutyl)naphth-1-ylmethyl]benzoate Using a similar procedure to that described in Example 5.d., except using morpholine instead of dimethylamine, methyl 3-methoxy-4-[7-(4-morpholino-4-oxobutyl)naphth-1-ylmethyl]benzoate was obtained (40%) as a yellow foam; MS(CI), m/e=462(M+H).

Analysis for C$_{28}$H$_{31}$NO$_5$.0.25 H$_2$O: Calculated: C, 72.16; H, 6.81; N, 3.01. Found: C, 71.72; H, 6.76; N, 3.55.

b. 3-Methoxy-4-[7-(4-morpholino-4-oxobutyl)naphth-1-ylmethyl]benzoic acid

Using a similar procedure to that described in Example 2.g., except starting from methyl 3-methoxy-4-[7-(4-morpholino-4-oxobutyl)naphth-1-ylmethyl]benzoate, 3-methoxy-4-[7-(4-morpholino-4-oxobutyl)naphth-1-ylmethyl]benzoic acid was obtained (75%) as a white powder; mp 160.0°–161° C.; MS(CI), m/e=448(M+H).

c. 3-Methoxy-N-(2-methylphenylsulfonyl)-4-[7-(4-morpholino-4-oxobutyl)naphth-1-ylmethyl]benzamide Using a similar procedure to that described in Example 2.h., except starting from 3-methoxy-4-[7-(4-morpholino-4-oxobutyl)naphth-1-ylmethyl]benzoic acid, the title compound was obtained (68%) as a white powder; mp 100.0°–102.0° C.; MS(CI), m/e=601(M+H).

Analysis for $C_{34}H_{36}N_2O_6S \cdot 0.5\ H_2O$: Calculated: C, 66.97; H, 6.12; N, 4.59. Found: C, 66.97; H, 6.04; N, 4.52.

EXAMPLE 8

3-Methoxy-N-(2-methylphenylsulfonyl)-4-[7-(2-methylpropylcarbamoyl)naphth-1-ylmethyl]benzamide a. Methyl 3-methoxy-4-[7-(2-methylpropylcarbamoyl)naphth-1-ylmethyl]benzoate Using a similar procedure to that described in Example 2.f., except using 2-methylpropylamine instead of 2-ethylbutylamine, methyl 3-methoxy-4-[7-(2-methylpropylcarbamoyl)naphth-1-ylmethyl]benzoate was obtained (81%) as a white solid; mp 174.0°–175.0° C.; MS(CI), m/e=405(M+H).

Analysis for $C_{25}H_{27}NO_4$: Calculated: C, 73.24; H, 6.76, N, 3.42. Found: C, 73.53; H, 6.69; N, 3.42.

b. 3-Methoxy-4-[7-(2-methylpropylcarbamoyl)naphth-1-ylmethyl]benzoic acid

Using a similar procedure to that described in Example 2.g., except starting from methyl 3-methoxy-4-[7-(2-methylpropylcarbamoyl)naphth-1-ylmethyl]-3-benzoate, 3-methoxy-4-[7-(2-methylpropylcarbamoyl)naphth-1-ylmethyl]benzoic acid was obtained (80%) as a light yellow powder; mp 253.5°–254.5° C.; MS(CI), m/e=392(M+H).

Analysis for $C_{24}H_{25}NO_4 \cdot 0.15\ H_2O$: Calculated: C, 73.13; H, 6.39; N, 3.55. Found: C, 73.14; H, 6.43; N, 3.46.

c. 3-Methoxy-N-(2-methylphenylsulfonyl)-4-[7-(2-methylpropylcarbamoyl)naphth-1-ylmethyl]benzamide Using a similar procedure to that described in Example 2.h., except starting from 3-methoxy-4-[7-(2-methylpropylcarbamoyl)naphth-1-ylmethyl]benzoic acid, the title compound was obtained (76%) as a white powder; mp 212.0°–213.5° C.; MS(CI), m/e=545(M+H).

Analysis for $C_{31}H_{32}N_2O_5S \cdot 1.0\ H_2O$: Calculated: C, 66.17; H, 6.09; N, 4.98. Found: C, 66.17; H, 5.82; N, 4.98.

EXAMPLE 9

4-[7-(2-Ethylbutylcarbamoyl)naphth-1-ylmethyl]-3-methoxy-N-(phenylsulfonyl)benzamide Using a similar procedure to that described in Example 2.h., except using phenylsulfonamide instead of 2-methylphenylsulfonamide, the title compound was obtained (69%) as a white powder; mp 210.0°–211.0° C.; MS(CI), m/e=559(M+H).

Analysis for $C_{32}H_{34}N_2O_5S \cdot 0.25\ H_2O$: Calculated: C, 68.24; H, 6.09; N, 4.97. Found: C, 68.29; H, 6.11; N, 5.16.

EXAMPLE 10

3-Methoxy-4-[7-(2-methylbutylcarbamoyl)naphth-1-ylmethyl]-N-(2-methylphenylsulfonyl)benzamide a. Methyl 3-methoxy-4-[7-(2-methylbutylcarbamoyl)naphth-1-ylmethyl]benzoate

Using a similar procedure to that described in Example 2.f., except using 2-methylbutylamine instead of 2-ethylbutylamine, methyl 3-methoxy-4-[7-(2-methylbutylcarbamoyl)naphth-1-ylmethyl]benzoate was obtained (69%) as a white powder; mp 134.0°–135.0° C.; MS(CI), m/e=419(M+H).

Analysis for $C_{26}H_{29}NO_4$: Calculated: C, 74.44; H, 6.97, N, 3.34. Found: C, 74.22; H, 6.92; N, 3.30.

b. 3-Methoxy-4-[7-(2-methylbutylcarbamoyl)naphth-1-ylmethyl]benzoic acid

Using a similar procedure to that described in Example 2.g., except starting from methyl 3-methoxy-4-[7-(2-methylbutylcarbamoyl)naphth-1-ylmethyl]benzoate, 3-methoxy-4-[7-(2-methylbutylcarbamoyl)naphth-1-ylmethyl]benzoic acid was obtained (78%) as a white solid; mp 220.0°–221.0° C.; MS(CI), m/e=405(M+H).

Analysis for $C_{25}H_{28}NO_4 \cdot 0.25\ H_2O$: Calculated: C, 73.24; H, 6.64; N, 3.42. Found: C, 73.58; H, 6.68; N, 3.37.

c. 3-Methoxy-4-[7-(2-methylbutylcarbamoyl)naphth-1-ylmethyl]-N-(2-methylphenylsulfonyl)benzamide Using a similar procedure to that described in Example 2.h., except starting from 3-methoxy-4-[7-(2-methylbutylcarbamoyl)naphth-1-ylmethyl]benzoic acid, the title compound was obtained (68%) as a white powder; mp 203.5°–204.5° C.; MS(CI), m/e=559(M+H).

Analysis for $C_{32}H_{34}N_2O_5S$: Calculated: C, 68.79; H, 6.13; N, 5.02. Found: C, 68.73; H, 6.13; N, 4.91.

EXAMPLE 11

4-(7-Carbamoylnaphth-1-ylmethyl)-3-methoxy-N-(2-methylphenylsulfonyl)benzamide a. Methyl 4-(7-carbamoylnaphth-1-ylmethyl)-3-methoxybenzoate

A mixture of methyl 4-(7-cyanonaphth-1-ylmethyl)-3-methoxybenzoate (394 mg), acetic acid (0.68 ml) and $BF_3$-etherate (0.22 ml) was heated to 120° C. for 15 min. After cooling, to the reaction mixture was added methylene chloride (50 ml) and 6N sodium hydroxide (3.5 ml) and it was stirred for 10 min. The aqueous layer was extracted with methylene chloride. The combined organic extract was washed (brine) and dried ($MgSO_4$). Evaporation and trituration with hot ethyl acetate afforded methyl 4-(7-carbamoylnaphth-1-ylmethyl)-3-methoxybenzoate (262 mg, 63%) as a white solid; mp 215.0°–216.5° C.; MS(CI), m/e=350(M+H).

b. 4-(7-Carbamoylnaphth-1-ylmethyl)-3-methoxybenzoic acid

Using a similar procedure to that described in Example 2.g., except starting from methyl 4-(7-carbamoylnaphth-1-ylmethyl)-3-methoxybenzoate, 4-(7-carbamoylnaphth-1-ylmethyl)-3-methoxybenzoic acid was obtained (76%) as a light yellow solid; mp 283.0°–285.0° C. MS(CI), m/e=335(M+H).

Analysis for $C_{20}H_{17}NO_4 \cdot 0.25\ H_2O$: Calculated: C, 70.68; H, 5.19; N, 4.12. Found: C, 70.98; H, 5.14; N, 4.13.

c. 4-(7-Carbamoylnaphth-1-ylmethyl)-3-methoxy-N-(2-methylphenylsulfonyl)benzamide Using a similar procedure to that described in Example 2.h., except starting from 4-(7-carbamoylnaphth-1-ylmethyl)-3-methoxybenzoic acid, the title compound was obtained (60%) as a white powder; mp 255.0°–256.0° C.; MS(CI), m/e=488(M+H).

Analysis for $C_{27}H_{24}N_2O_5S \cdot 0.25\ H_2O$: Calculated: C, 65.77; H, 5.01; N, 5.68. Found: C, 65.68; H, 5.02; N, 5.83.

EXAMPLE 12

4-[7-(4-Dimethylcarbamoylbutyl)naphth-1-ylmethyl]-3-methoxy-N-(2-methylphenylsulfonyl)benzamide a. Methyl 4-[7-(1-hydroxyallyl)naphth-1-ylmethyl]-3-methoxybenzoate

A solution of methyl 4-(7-formylnaphth-1-ylmethyl)-3-methoxybenzoate (2.006 g) in tetrahydrofuran (60 ml) under nitrogen, at −78° C., was treated with 1M vinylmagnesium bromide in tetrahydrofuran (6.3 ml, 6.3 mmol) and allowed to warm to 0° C. over 1.5 hours. After stirring at 0° C. for 30 min, saturated ammonium chloride (30 ml) was added. The mixture was extracted with ethyl acetate, and the organic layer was washed (water, brine) and dried (MgSO$_4$). Evaporation afforded methyl 4-[7-(1-hydroxyallyl)naphth-1-ylmethyl]-3-methoxybenzoate (2.6 g, quantitative) as a light brown syrup. A 200 mg sample was purified by flash chromatography, eluting with 3:7 ethyl acetate:petroleum ether, to afford methyl 4-[7-(1-hydroxyallyl)-naphth-1-ylmethyl]-3-methoxybenzoate as an orange syrup; MS(EI), m/e=36Z (M+.).

b. Methyl 4-[7-[4-(dimethylcarbamoyl)but-1-enyl]naphth-1-ylmethyl]-3-methoxybenzoate A mixture of methyl 4-[7-(1-hydroxyallyl)naphth-1-ylmethyl]-3-methoxybenzoate (2.4 g), N,N-dimethylacetamide dimethyl acetal (1.62 ml) and toluene (50 ml) was refluxed for 12 hours. Evaporation and flash chromatgraphy, eluting with a gradient of 1) 3:3:2 petroleum ether:methylene chloride:ethyl acetate, 2) 1:1:1 petroleum ether:methylene chloride:ethyl acetate, and 3) 6:6:7 petroleum ether:methylene chloride:ethyl acetate, afforded methyl 4-[7-[4-(dimethylcarbamoyl)but-1-enyl]naphth-1-ylmethyl]-3-methoxybenzoate (90%) as a light yellow syrup; MS(CI), m/e=432(M+H).

c. Methyl 4-[7-(4-dimethylcarbamoylbutyl)naphth-1-ylmethyl]-3-methoxybenzoate A mixture of methyl 4-[7-[4-(dimethylcarbamoyl)but-1-enyl]naphth-1-ylmethyl]-3-methoxybenzoate (1.1 g), 10% w/w palladium-on-carbon/50% water (110 mg) and ethyl acetate (10 ml) was hydrogenated under atmospheric pressure for 4 hours. Filtration through diatomaceous earth with ethyl acetate wash and evaporation afforded methyl 4-[7-(4-dimethylcarbamoylbutyl)-naphth-1-ylmethyl]-3-methoxybenzoate (1.15 g, quantitative) as a light yellow syrup; MS(CI), m/e=434(M+H).

d. 4-[7-(4-Dimethylcarbamoylbutyl)naphth-1-ylmethyl]-3-methoxybenzoic acid

Using a similar procedure to that described in Example 2.g., except starting from methyl 4-[7-(4-dimethylcarbamoylbutyl)naphth-1-ylmethyl]-3-methoxybenzoate, 4-[7-(4-dimethylcarbamoylbutyl)naphth-1-ylmethyl]-3-methoxybenzoic acid was obtained (81%) as a white powder; mp 125.0°–127.0° C.; MS(CI), m/e=420(M+H).

Analysis for C$_{26}$H$_{29}$NO$_4$: Calculated: C, 74.43; H, 6.96; N, 3.33. Found: C, 74.03; H, 6.92; N, 3.28.

e. 4-[7-(4-Dimethylcarbamoylbutyl)naphth-1-ylmethyl]-3-methoxy-N-(2-methylphenylsulfonyl)benzamide Using a similar procedure to that described in Example 2.h., except starting from methyl 4-[7-(4-dimethylcarbamoylbutyl)naphth-1-ylmethyl]-3-methoxybenzoate, the title compound was obtained (84%) as a light tan powder; mp 88.0°–93.0° C.; MS(CI), m/e=573(M+H).

Analysis for C$_{33}$H$_{36}$N$_2$O$_5$S.0.25 H$_2$O:
Calculated: C, 68.66; H, 6.371 N, 4.85. Found: C, 68.53; H, 6.34; N, 5.22.

EXAMPLE 13

N-(2-Bromophenylsulfonyl)-4-[7-(4-dimethylcarbamoylbutyl)naphth-1-ylmethyl]-3-methoxybenzamide Using a similar procedure to that described in Example 12.e., except using 2-bromophenylsulfonamide, the title compound was obtained (98%) as a light tan powder; mp 91.0°–97.0° C.; MS(CI), m/e=639,637(M+H).

Analysis for C$_{32}$H$_{33}$BrN$_2$O$_5$S.0.25 H$_2$O: Calculated: C, 59.85; H, 5.25; N, 4.36. Found: C, 59.70; H, 5.25; N, 4.30.

EXAMPLE 14

The following illustrates representative pharmaceutical dosages forms which may be used for the therapeutic or prophylactic administration of a compound of formula I or of a pharmaceutically acceptable salt thereof (hereinafter referred to as 'Compound X'):

| (i) | Tablet 1 | mg/tablet |
|---|---|---|
| | 'Compound X' | 100.0 |
| | Lactose | 182.75 |
| | Croscarmellose Sodium | 12.0 |
| | Starch | 2.25 |
| | Magnesium stearate | 3.0 |
| (ii) | Tablet 2 | mg/tablet |
| | 'Compound X' | 20.0 |
| | Microcrystalline cellulose | 420.0 |
| | Polyvinylpyrrolidone | 14.0 |
| | Starch | 43.0 |
| | Magnesium stearate | 3.0 |
| (iii) | Capsule | mg/capsule |
| | 'Compound X' | 10.0 |
| | Lactose | 488.5 |
| | Magnesium stearate | 1.5 |
| (iv) | Injection 1 | (10 mg/ml) |
| | 'Compound X' (free acid form) | 1.0% w/v |
| | Sodium phosphate | 3.6% w/v |
| | 0.1M Sodium hydroxide solution | 15.0% w/v |
| | Water for injection ... to 100% | |
| (v) | Injection 2 (buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 0.38% w/v |
| | Water for injection ... to 100% | |
| (vi) | Aerosol | mg/ml |
| | 'Compound X' | 0.2 |
| | Sorbitan trioleate | 0.27 |
| | Trichlorofluoromethane | 70.0 |
| | Dichloridifluoromethane | 280.0 |
| | Dichlorotetrafluoroethane | 1094.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.
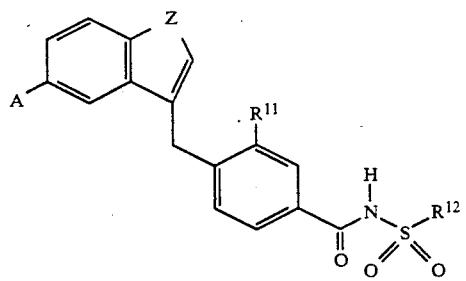
I
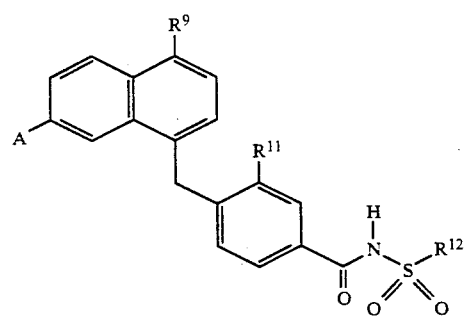
Ia
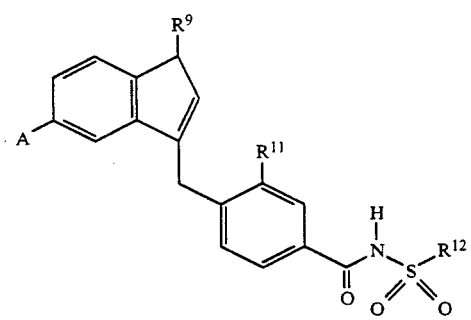
Ib
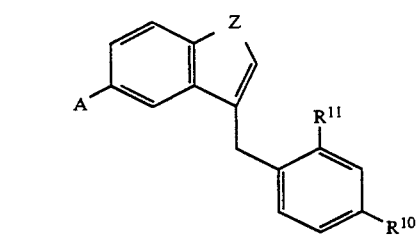
III
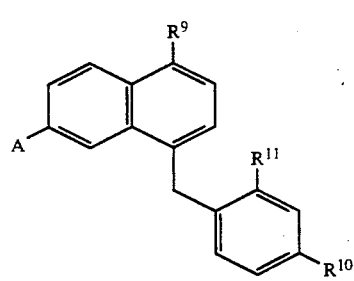
IIIa
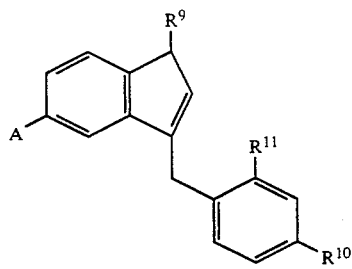
IIIb
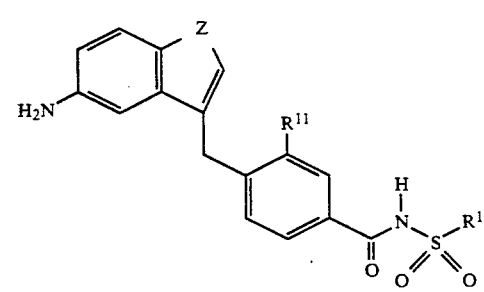
IV
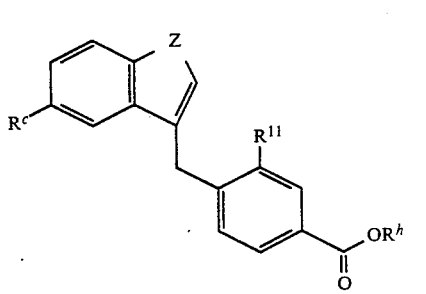
V
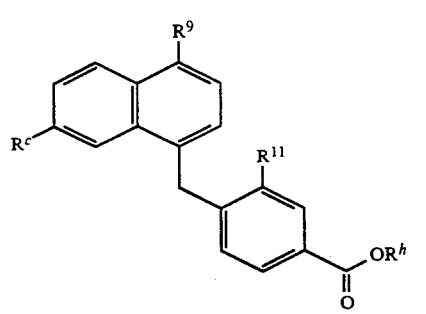
Va
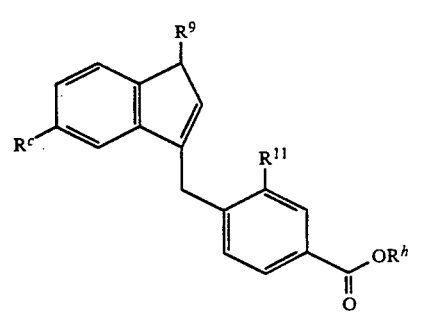
Vb Scheme Ia
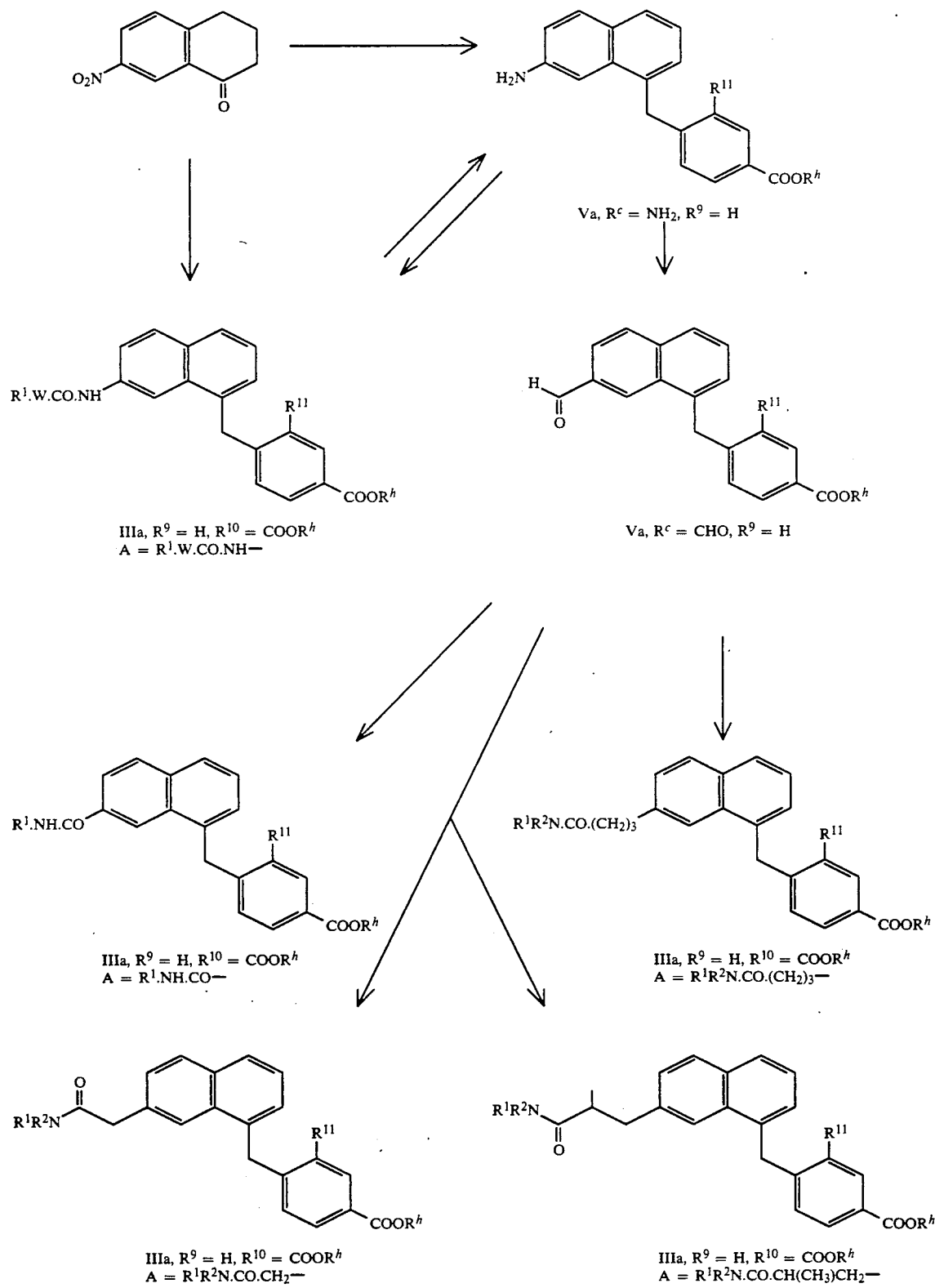

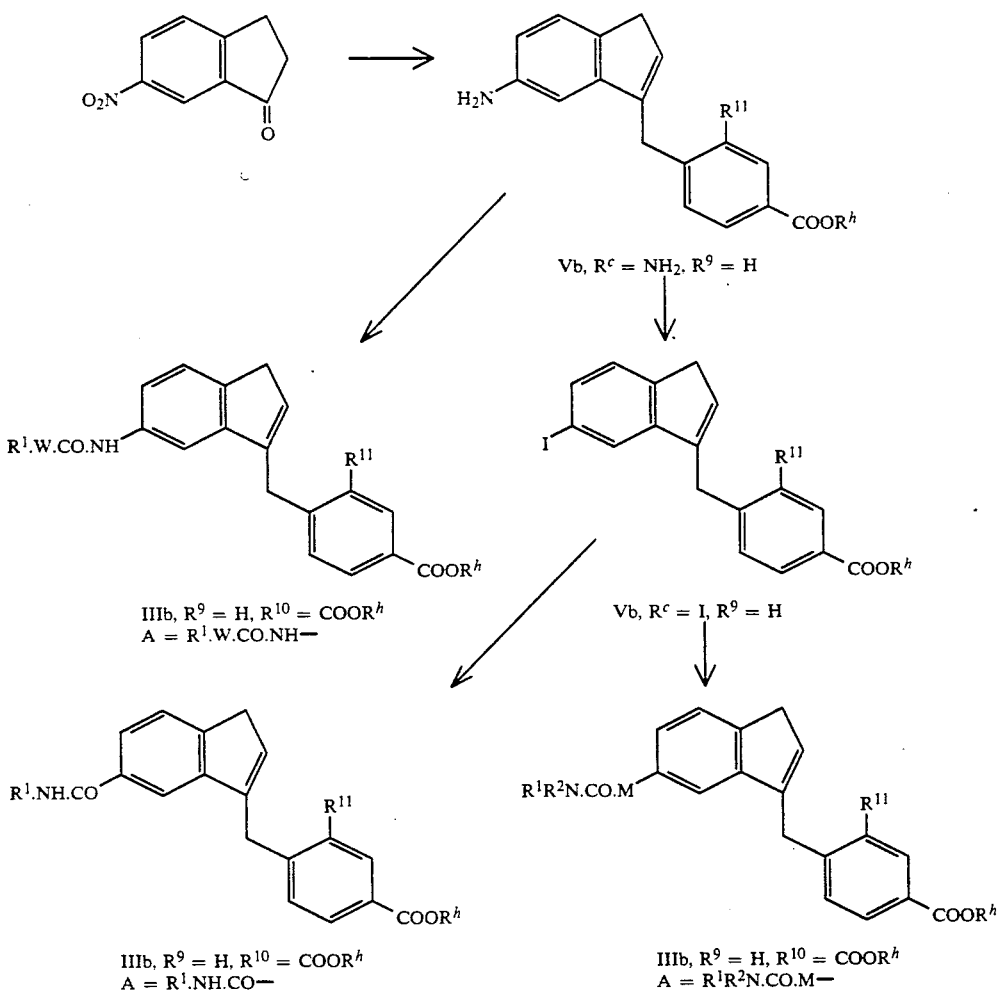

What is claimed is:

1. A compound of formula I

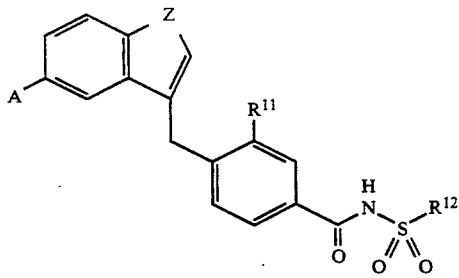

wherein
—Z— is selected from a group consisting of (a) —C(R⁹)=CH— and (b) —CH(R⁹)—;
A is an amidic side chain selected from a group consisting of
(i) an acylamino group of formula R¹.W.CO.NH-,
(ii) a carboxamido group of formula R¹.NH.CO-, and
(iii) an aliphatic carboxamido group of formula R¹R²N.CO.M-;
and wherein $R^1$ is hydrogen or (1-6C)alkyl optionally containing a double or triple bond and
$R^2$ is selected from a group consisting of hydrogen, (1-6C)alkyl optionally containing a double or triple bond, (3-6C)cycloalkyl, (3-6C)cycloalkyl(1-3-C)alkyl and phenyl, in which a cycloalkyl group or the cycloalkyl portion of a cycloalkylalkyl group may contain a double bond and may bear 1 or 2 (1-3C)alkyl groups, or
$R^1$ and $R^2$, together with the nitrogen atom to which they are attached, form a pyrrolidino, piperidino, piperazine, 4-((1-3C)alkyl)piperazino, or morpholino group;
M is a (1-5C)alkylene group;
W is oxy, imino or a single bond;
$R^9$ is selected from a group consisting of hydrogen, (1-6C)alkyl optionally containing a double or triple bond, (1-5C)alkoxy, (1-6C)alkanoyl and halogeno;
$R^{11}$ is hydrogen or (1-4C)alkoxy; and
$R^{12}$ is phenyl, which may bear 2 or 2 substituents selected from a group consisting of halogeno, methyl and (1-4C)alkoxy;
or a salt thereof.

2. A compound as claimed in claim 1 wherein $R^1$ is hydrogen, methyl, ethyl, propyl, isopropyl, butyl, 1-methylpropyl, 2-methylpropyl, pentyl, 1-ethylpropyl, 3-methylbutyl, hexyl, 4-methylpentyl, allyl, 2-methylprop-2-enyl, 3-methylbut-3-enyl, or 2-propynyl;

$R^2$ is hydrogen, methyl, ethyl, propyl, isopropyl, butyl, 1-methylpropyl, 2-methylpropyl, pentyl, 1-ethylpropyl, 3-methylbutyl, hexyl, 4-methylpentyl, allyl, 2-methylprop-2-enyl, 3-methylbut-3-enyl, 2-propynyl, cyclopropyl, cyclobutyl, cyclopentyl, cyclohexyl, cyclopentenyl, cyclohexenyl, methylcyclobutyl, cyclopropylmethyl, cyclobutylmethyl, cyclopentylmethyl, cyclohexylmethyl, 1-cyclopentylethyl, 2-cyclopentylethyl, or methylcyclopentylethyl; or $R^1$ and $R^2$, together with the nitrogen atom to which they are attached, form a pyrrolidino, piperazino morpholino or piperazine group, which piperazino group may bear a methyl, ethyl or isopropyl substituent at the 4-position;

M is methylene, ethan-1,2-diyl, propan-1,3-diyl, propan-1,2-diyl, 2-methylpropan-1,2-diyl, butan-1,3-diyl or butan-1,4-diyl;

$R^9$ is hydrogen, methyl, ethyl, propyl, isopropyl, butyl, 1-methylpropyl, 2-methylpropyl, pentyl, 1-ethylpropyl, 3-methylbutyl, hexyl, 4-methylpentyl, allyl, 2-methylprop-2-enyl, 3-methylbut-3-enyl, 2-propynyl, methoxy, ethoxy, propoxy, 2-methylpropyloxy, butoxy, pentoxy, 3-methylbutoxy, acetyl, propanoyl, butanoyl, 2-methylpropanoyl, 3-methylbutanoyl, bromo or chloro;

$R^{11}$ is methoxy, ethoxy or propoxy; and $R^{12}$ is phenyl which may bear a methyl, chloro, bromo, methoxy or ethoxy substituent.

3. A compound as claimed in claim 2 wherein $R^{12}$ bears a single substituent at the 2-position.

4. A compound as claimed in claim 2 wherein A is cyclopentylacetamido, carboxamido, 2-methylpropylcarboxamido, 2-methylbutylcarboxamido, 2-ethylbutylcarboxamido, 2-(propylcarbamoyl)propyl, 3-(dimethylcarbamoyl)propyl, 4-(dimethylcarbamoyl)butyl or 4-morpholino-4-oxobutyl.

5. A compound as claimed in any one of claims 1–4 wherein $R^9$ is hydrogen.

6. A compound as claimed in claim 1 selected from 4-[7-(cyclopentylacetamido)naphth-1-ylmethyl]-3-methoxy-N-(2-methylphenylsulfonyl)benzamide; 4-[7-(3-dimethylcarbamoylpropyl)naphth-1-ylmethyl]-3-methoxy-N-(2-methylphenylsulfonyl)benzamide; 4-[6-(cyclopentylacetamido-3H-inden-1-ylmethyl]-3-methoxy-N-(2-methylphenylsulfonyl)benzamide; 3-methoxy-N-(2methylphenylsulfonyl)-4-[7-(2-methylpropylcarbamoyl)naphth-1-ylmethyl]benzamide; and 3-methoxy-4-[7-methylbutylcarbamoyl)naphth-1-ylmethyl]-N-(2-methylphenylsulfonyl)benzamide; or a pharmaceutically acceptable salt thereof.

7. A salt as claimed in claim 1 wherein said salt is made with a base forming a physiologically acceptable cation.

8. A pharmaceutical composition comprising a leukotriene antagonizing amount of a compound of claim 1 or a pharmaceutically acceptable salt thereof and a pharmaceutically acceptable diluent or carrier.

9. A composition as claimed in claim 8 wherein said composition is in the form of a liquid or powdered aerosol.

10. A method of antagonizing the action of at least one type of leukotriene in a mammal requiring such treatment comprising administering to said mammal an effective amount of a compound of claim 1.

11. A method for the treatment of a selected allergic or inflammatory disorder in a mammal in need of such treatment comprising administering an effective amount of a compound of claim 1 to such mammal.

* * * * *

UNITED STATES PATENT AND TRADEMARK OFFICE
CERTIFICATE OF CORRECTION

PATENT NO. : 5,095,038
DATED : March 10, 1992
INVENTOR(S) : Brown et al.

It is certified that error appears in the above-identified patent and that said Letters Patent is hereby corrected as shown below:

On the title page, item 56, Foreign Patent Documents "10/1985" should read --04/1986--.

Column 29, line 66, "carboxamido group" should read --carboxamidic group--.

Column 30, line 61, "2 or 2 substituents" should read --1 or 2 substituents--.

Column 32, line 13, "methoxy-N-(2methylphenylsulfonyl)" should read --methoxy-N-(2-methylphenylsulfonyl)--.

Column 32, line 15, "[7-methylbutylcarbamoyl)" should read --[7-(2-methylbutylcarbamoyl)--.

UNITED STATES PATENT AND TRADEMARK OFFICE
CERTIFICATE OF CORRECTION

PATENT NO. : 5,095,038
DATED : March 10, 1992
INVENTOR(S) : Brown et al

It is certified that error appears in the above-indentified patent and that said Letters Patent is hereby corrected as shown below:

Column 32, line 15, "[7-methylbutylcarbamoyl)" should read --[7-(2-methylbutylcarbamoyl)--.

Signed and Sealed this

Eleventh Day of April, 1995

Attest:

BRUCE LEHMAN

Attesting Officer    Commissioner of Patents and Trademarks